(12) United States Patent
Chelak et al.

(10) Patent No.: US 10,376,684 B2
(45) Date of Patent: Aug. 13, 2019

(54) MULTI-FUNCTIONAL MEDICAL SAMPLING PORT AND METHOD OF USING SAME

(71) Applicant: NP Medical Inc., Clinton, MA (US)

(72) Inventors: Todd Chelak, Westborough, MA (US); Ian Kimball, Townsend, MA (US)

(73) Assignee: NP MEDICAL INC., Clinton, MA (US)

( * ) Notice: Subject to any disclaimer, the term of this patent is extended or adjusted under 35 U.S.C. 154(b) by 407 days.

(21) Appl. No.: 15/107,589

(22) PCT Filed: Dec. 18, 2014

(86) PCT No.: PCT/US2014/071203
§ 371 (c)(1),
(2) Date: Jun. 23, 2016

(87) PCT Pub. No.: WO2015/100135
PCT Pub. Date: Jul. 2, 2015

(65) Prior Publication Data
US 2016/0325085 A1    Nov. 10, 2016

Related U.S. Application Data

(60) Provisional application No. 61/921,184, filed on Dec. 27, 2013.

(51) Int. Cl.
*A61M 39/02*    (2006.01)
*F16K 7/20*    (2006.01)
(Continued)

(52) U.S. Cl.
CPC ...... *A61M 39/0247* (2013.01); *A61M 39/045* (2013.01); *A61M 39/223* (2013.01);
(Continued)

(58) Field of Classification Search
CPC .............. A61M 5/16813; A61M 39/10; A61M 39/223; A61M 39/225; A61M 39/26;
(Continued)

(56) References Cited

U.S. PATENT DOCUMENTS 4,915,687 A * 4/1990 Sivert .................... A61M 39/02
137/605
5,782,816 A * 7/1998 Werschmidt .......... A61M 39/02
137/903
(Continued)

FOREIGN PATENT DOCUMENTS

DE    10 2006 044 722    4/2008
EP    2 832 398    2/2015
(Continued)

OTHER PUBLICATIONS

Melitta Messmer, Authorized officer European Patent Office, International Search Report—Application No. PCT/US2014/071203, dated Jul. 21, 2015, together with the Written Opinion of the International Searching Authority, 18 pages.
(Continued)

*Primary Examiner* — Bhisma Mehta
*Assistant Examiner* — William R Frehe
(74) *Attorney, Agent, or Firm* — McCarter & English, LLP; Jonathan C. Lovely (57) ABSTRACT

A medical port includes a hub having a body forming a hub chamber for containing a fluid, and a proximal opening to the hub chamber for receiving a medical implement. The port also has a valve member, a first radial fluid channel, and a second radial fluid channel. The valve member is located within the hub chamber, has a radial portion, and closes the proximal opening when the medical port is in a closed mode. The first and second radial fluid channels are in fluid communication with the hub chamber when the medical port
(Continued)

is in the closed mode. The radial portion of the valve member restricts fluid communication between the first radial fluid channel and the hub chamber when the medical port is in an open mode.

7 Claims, 11 Drawing Sheets

(51) Int. Cl.
*F16K 7/00* (2006.01)
*A61M 39/04* (2006.01)
*A61M 39/22* (2006.01)
*A61M 39/24* (2006.01)
*A61M 39/26* (2006.01)
*A61M 39/10* (2006.01)

(52) U.S. Cl.
CPC ............ *A61M 39/24* (2013.01); *A61M 39/26* (2013.01); *F16K 7/00* (2013.01); *F16K 7/20* (2013.01); *A61M 2039/0202* (2013.01); *A61M 2039/027* (2013.01); *A61M 2039/0276* (2013.01); *A61M 2039/1072* (2013.01); *A61M 2039/1083* (2013.01); *A61M 2039/1088* (2013.01); *A61M 2039/2433* (2013.01)

(58) Field of Classification Search
CPC ... A61M 2039/1072; A61M 2039/2433; Y10S 137/903; F16K 7/20; F16K 11/022; F16K 7/04; F16K 7/06; F16K 7/16; F16K 7/14
USPC .............................................. 251/149.1, 331
See application file for complete search history.

(56) References Cited

U.S. PATENT DOCUMENTS

| | | | |
|---|---|---|---|
| 6,032,690 A * | 3/2000 | Weissfloch | F16K 7/126 137/599.08 |
| 6,220,299 B1 * | 4/2001 | Arvidsson | F16K 7/16 137/329.05 |
| 8,298,196 B1 * | 10/2012 | Mansour | A61M 39/04 604/256 |
| 2002/0193752 A1 | 12/2002 | Lynn | |
| 2006/0027270 A1 * | 2/2006 | Truitt | A61M 39/02 137/843 |
| 2006/0089603 A1 | 4/2006 | Truitt et al. | |
| 2012/0067429 A1 * | 3/2012 | Mosler | A61J 1/2089 137/1 |
| 2013/0060205 A1 * | 3/2013 | Mansour | A61M 39/223 604/248 |
| 2014/0014207 A1 * | 1/2014 | Ziv | A61M 39/223 137/625.46 |
| 2015/0045746 A1 * | 2/2015 | Macy, Jr. | A61M 39/26 604/246 |
| 2016/0369915 A1 * | 12/2016 | Vu | F16K 41/12 |

FOREIGN PATENT DOCUMENTS

| | | |
|---|---|---|
| WO | WO 2006/025054 | 3/2006 |
| WO | WO 2009/029751 | 3/2009 |
| WO | WO 2011/100187 | 8/2011 |
| WO | WO 2013/146753 | 10/2013 |

OTHER PUBLICATIONS

International Searching Authority, Annex to Form PCT/ISA/206 Communication Relating to the Results of the Partial International Search—Application No. PCT/US2014/071203, dated Apr. 16, 2015, 3 pages.

* cited by examiner

MULTI-FUNCTIONAL MEDICAL SAMPLING PORT AND METHOD OF USING SAME

PRIORITY

This patent application claims priority from U.S. Provisional Patent Application No. 61/921,184, filed Dec. 27, 2013, entitled, "Multi-Functional Sampling Port," and naming Todd Chelak and Ian Kimball as inventors, the disclosure of which is incorporated herein, in its entirety, by reference.

TECHNICAL FIELD

The invention generally relates to fluid management devices and, more particularly, the invention relates to a sampling port within arterial or venous fluid transfer sets.

BACKGROUND ART

There are a number of fluid transfer applications (e.g., applications in which fluid is being administered to and/or drawn from a patient) that require a medical practitioner to take a sample of the blood being drawn from the patient and/or the fluid being transferred to the patient. In such applications, the medical practitioner may utilize a fluid transfer set (e.g., a tubing set) that includes monitoring lines that are, in turn, connected (e.g., at the downstream end) to a catheter placed in the patient's artery or vein. A fluid source (e.g. saline bag) is typically connected to the upstream end of the monitoring line so that the monitoring line may be flushed via a saline drip.

The fluid transfer set may also include a sample port that that is in fluid communication with (and creates fluid communication between) the downstream and upstream ends of the monitoring line. The sample port allows the medical practitioner to draw a sample of the blood or fluid without removing the catheter from the patient or otherwise disconnecting the components of the fluid transfer set. However, when sampling a fluid (e.g. blood) from a conventional T-shaped sampling port, the downstream and upstream openings to the sampling port (e.g., a chamber of the port) are left unrestricted to fluid flow. Therefore, blood may be drawn from the upstream portion of the monitoring line where the blood may have been sitting in the system for some time and/or diluted with saline. Such a blood sample may produce erroneous results and is, therefore, not preferred for lab analysis. To avoid taking a diluted blood/fluid sample, some prior art systems use stopcocks to close off upstream fluid communication during sampling. However, stopcocks add cost and often require substantial manipulation from the medical practitioner during use.

Furthermore, in some critical care applications, the medical practitioner may be required to regularly monitor the patient's arterial or venous blood pressure. In such applications, the fluid transfer set may also include a pressure transducer (located upstream from the sampling port) that connects to a display that graphically shows a read-out of the arterial or venous blood pressure. To avoid negative interference with the pressure measurement that may be caused by certain components within the sampling port (e.g. resilient silicone septum), some prior art systems use stopcocks to close off fluid communication to portions of the sampling port during pressure measurement. However, as mentioned previously, stopcocks add cost and often require substantial manipulation from the medical practitioner during use.

SUMMARY OF THE EMBODIMENTS

In a first embodiment of the invention there is provided a medical port having an open mode that permits fluid sampling and a closed mode that prevents fluid sampling. The medical port may have a hub with a body forming a hub chamber for containing a fluid. The hub may also have a proximal opening to the hub chamber for receiving a medical implement (e.g., for fluid sampling and/or transfer to/from the patient). The medical port may also include a valve member (e.g., a resilient member), a first radial fluid channel and a second radial fluid channel. The valve member may be located within the hub chamber, and may close the proximal opening when the medical port is in the closed mode. The first and second radial fluid channels may be in fluid communication with the hub chamber when the medical port is in the closed mode. A radial portion of the valve member may restrict fluid communication between the first radial fluid channel and the hub chamber when the medical port is in the open mode (e.g., the radial portion may fluidly disconnect the first radial fluid channel and the hub chamber when the medical port is in the open mode).

In some embodiments, the valve member may include a flow disrupter that interacts with fluid entering the hub chamber when the medical port is in the closed mode (e.g., to flush the hub chamber). The flow disrupter may be a ring extending radially outward from the valve member, a helical groove within the valve member, and/or a raised helical structure within the valve member. The valve member may also include a notch located within a proximal portion of the valve member. The notch may allow the proximal portion to collapse after insertion of the medical implement into the proximal opening. The proximal surface of the valve member may include channel(s) configured to facilitate fluid communication between the medical implement and the hub chamber.

Additionally or alternatively, the valve member may have a normally closed slit extending through a width of the valve member. The normally closed slit may open as the medical port transitions from the closed mode to the open mode. The normally closed slit may form at least part of a fluid flow path between the second radial fluid channel and the proximal opening when the medical port is in the open mode. In such embodiments, the valve member may expand radially as the medical port transitions from the closed mode to the open mode.

The hub body may have a non-symmetrical base that interacts with the distal end of the valve member to cause the valve member to deform towards the first radial fluid channel as the medical port transitions from the closed mode to the open mode. For example, the first radial fluid channel may be located on a first side of the medical port, and the non-symmetrical base may have a raised portion located on a second/opposite side of the medical port. The first radial fluid channel may be aligned with the second radial fluid channel. Alternatively, the first radial fluid channel may be offset from the second radial fluid channel. For example, the first radial fluid channel may be located a first distance from the base of the hub body, and the second radial fluid channel may be located a second/shorter distance from the base (e.g., the first distance may be greater than the second). The first and second radial fluid channels may be in fluid communication with each other when the medical port is in the closed mode.

In additional embodiments, the radial portion of the valve member may include an interacting surface that interacts with the opening of the first radial fluid channel to restrict the fluid flow through the first radial fluid channel when the medical port is in the open mode. The interacting surface may include a protrusion that contacts the opening when the medical port is in the open mode. Additionally or alternatively, the interacting surface may be contoured and/or flat. A portion of the inner wall of the hub body may be configured to receive at least a portion of the interacting surface, and/or the inner wall of the hub body may have a protrusion that mates with at least a portion of the interacting surface. In some embodiments, the opening of the first radial fluid channel may receive at least a portion of the interacting surface.

The proximal surface of the valve member may be swabbable when the medical port is in the closed mode. Additionally, the valve member may include a valve base that rotationally constrains the valve member when the medical port is in the closed mode.

In further embodiments, a method includes connecting a medical port to a patient. The medical port may have a hub having (1) a body forming a hub chamber for containing a fluid, and (2) a proximal opening to the hub chamber. The medical port may also have a valve member located within the hub chamber, and a first and second radial fluid channel. The valve member may have a radial portion, and may close the proximal opening when the medical port is in a closed mode. The first and second radial fluid channels may be in fluid communication with the hub chamber when the medical port is in the closed mode.

The method may also include inserting a medical implement through the proximal opening to contact the valve member, moving the medical implement distally within the hub body to transition the medical port from the closed mode to the open mode, and transferring fluid between the medical implement and the patient through the medical port. The valve member may deform as the medical port transitions from the closed mode to the open mode. The radial portion may restrict fluid communication between the first radial channel and the hub chamber when the medical port is in the open mode (e.g., the radial portion may fluidly disconnect the first radial fluid channel and the hub chamber when the medical port is in the open mode).

In some embodiments, the valve member may include a flow disrupter that is configured to interact with fluid entering the hub chamber when the medical port is in the closed mode (e.g., to flush the hub chamber). The flow disrupter may be a ring extending radially outward from the valve member, a helical groove within the valve member, and/or a raised helical structure within the valve member. Additionally or alternatively, the valve member may include a notch located within a proximal portion of the valve member. The proximal portion of the valve member may collapse after insertion of a medical implement into the proximal opening. The proximal surface of the valve member may include at least one channel configured to facilitate fluid communication between the medical implement and the hub chamber when the medical port is in the open mode.

The valve member may have a normally closed slit extending through a width of the valve member. The normally closed slit may open as the medial port transitions from the closed mode to the open mode, and may also form at least part of a fluid flow path between the second radial fluid channel and the proximal opening when the medical port is in the open mode. In some embodiments, the valve member may expand radially as the medical port transitions from the closed mode to the open mode.

The hub body may include a non-symmetrical base configured to interact with a distal end of the valve member to cause the valve member to deform towards the first fluid channel as the medical port transitions from the closed mode to the open mode. For example, the first fluid channel may be located on a first side of the medical port, and the non-symmetrical base may include a raised portion located on a second/opposite side of the medical port. The first fluid channel may be offset from the second fluid channel such that the first radial fluid path is located first distance from a base of the hub body and the second radial fluid path is located a second distance from the base. The first distance may be greater than the second distance.

In still further embodiments, the radial portion of the valve member may include an interacting surface that interacts with an opening of the first radial fluid channel to restrict fluid flow through the first radial fluid channel when the medical port is in the open mode. The interacting surface may include a protrusion that contacts the opening when the medical port is in the open mode. Additionally or alternatively, the interacting surface may be contoured or flat. A portion of an inner wall of the hub body may (1) be configured to receive at least a portion of the interacting surface, and/or (2) include a protrusion that mates with at least a portion of the interacting surface. The opening of the first radial fluid channel may be configured to receive at least a portion of the interacting surface. The valve member may also include a valve base that rotationally constrains the valve member when the medical port is in the closed mode.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, a medical sampling port has a valve member that seals a proximal opening within a body of the sampling port when the sampling port is in its closed mode (i.e., sealed). When in its open mode (i.e., unsealed), a portion of the valve member restricts fluid communication between a radial fluid channel and a fluid chamber within the sampling port. In this manner, some embodiments of the present invention allow blood sampling of a monitoring line, and reduce the risk (and in some instances prevent) of drawing fluid from the upstream portion of the monitoring line into the chamber during sampling.

Figure 1A:
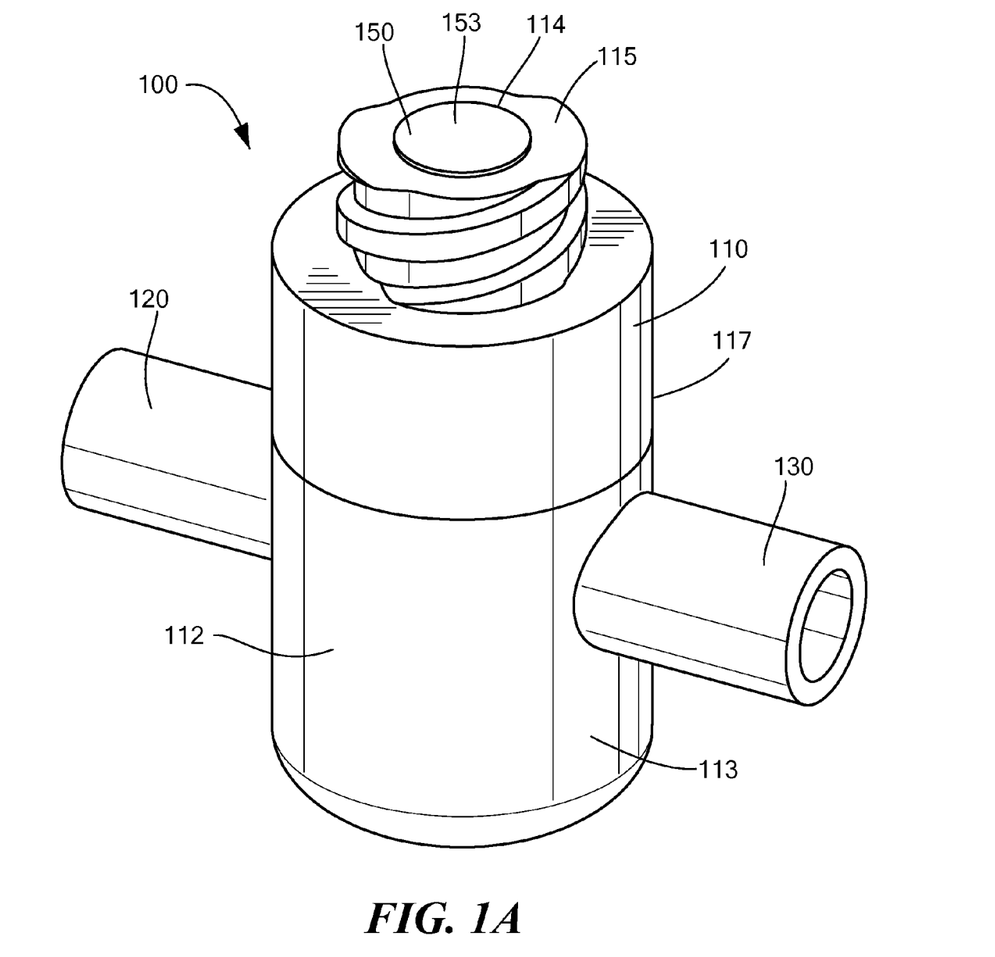
FIG. 1A schematically shows a perspective view of a sampling port, in accordance with various embodiments of the present invention.

FIG. 1A schematically shows a perspective view of a sampling port 100 configured in accordance with illustrative embodiments of the invention. The sampling port 100 includes a hub portion 110 with a first radial fluid channel (e.g., an inlet 120) and second radial fluid channel (e.g., an outlet 130) extending out from the body 112 of the hub portion 110. The inlet 120 and outlet 130 may each be connected to a section of tubing (not shown). For example, the sampling port 100 may be part of a fluid transfer set used to transfer fluids to a patient and/or draw blood from the patient. To that end, the inlet 120 may be connected (e.g., welded, glued, press-fit, etc.) to a section of tubing that leads to a drip chamber and a fluid bag (e.g., containing medicine or other fluid being intravenously supplied to a patient). Conversely, the outlet 130 may be connected to a section of tubing that leads to a catheter or needle inserted into the patient (not shown). To facilitate fluid flow into and out of the inlet 120 and outlet 130, the hub portion 110 may include an inlet opening 122 and an outlet opening 132 within the wall of the hub portion 110 (FIG. 2A).

Figure 1B:
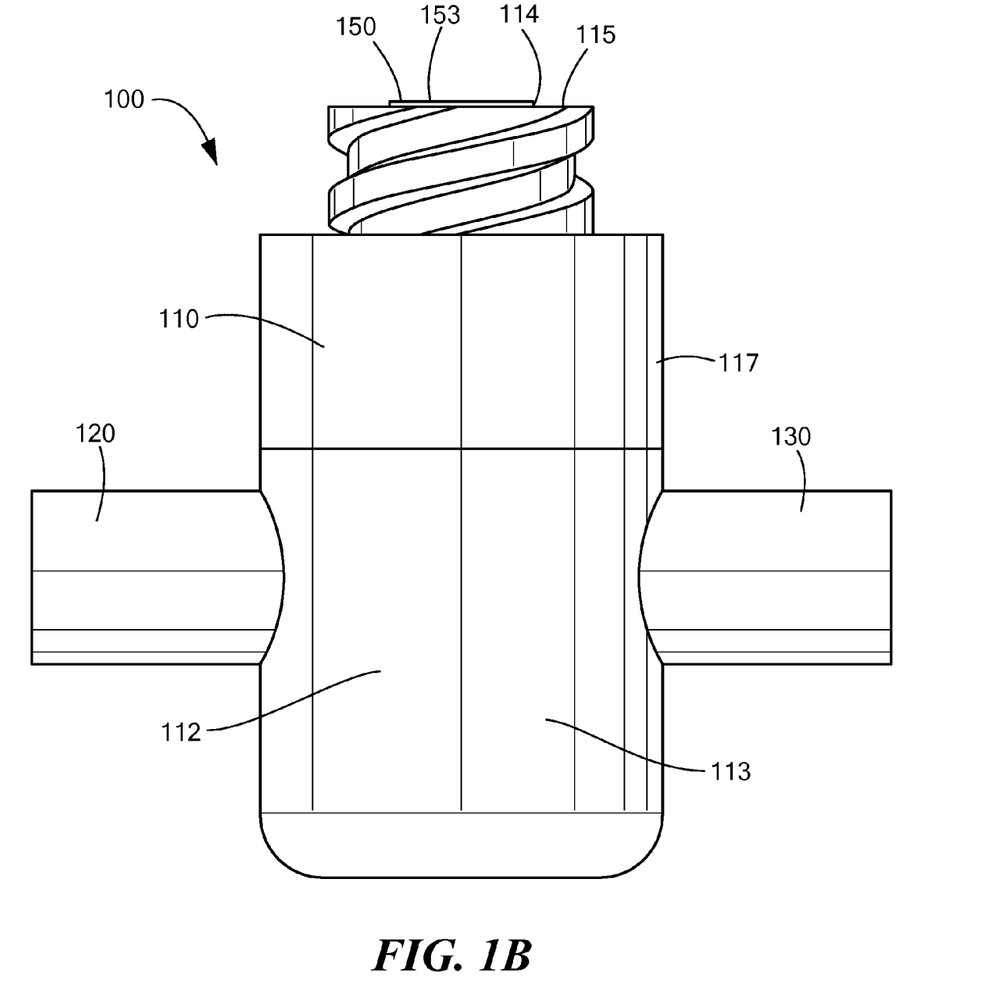
FIG. 1B schematically shows a side view of the sampling port shown in FIG. 1A, in accordance with various embodiments of the present invention.
Figure 1C:
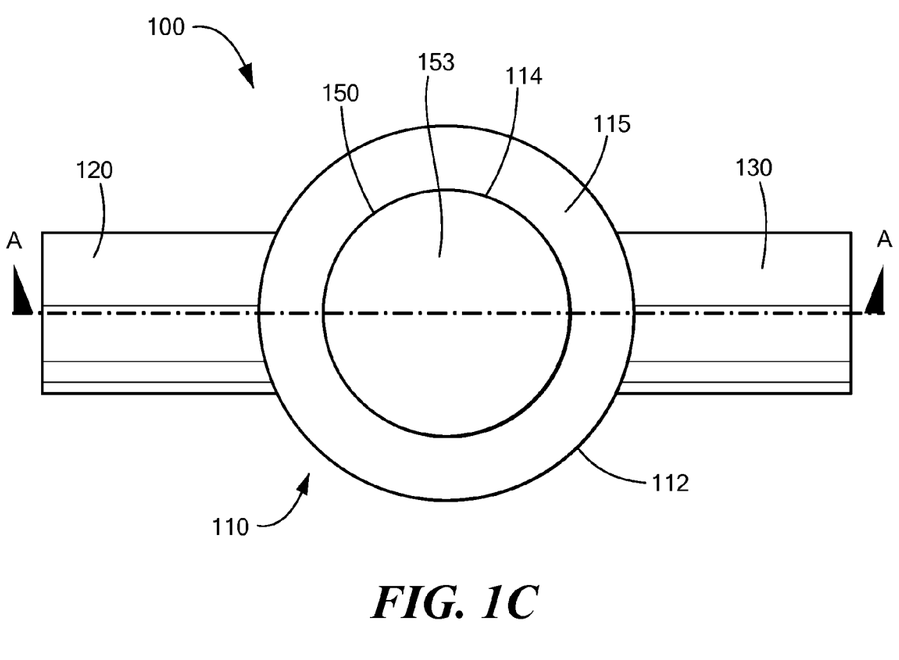
FIG. 1C schematically shows a top view of the sampling port shown in FIG. 1A, in accordance with various embodiments of the present invention.

It is important to note that, although FIGS. 1A and 1B show the inlet 120 and 130 aligned with one another such that their longitudinal axes are in-line/coincident with one another, other embodiments may have a different inlet 120 and outlet 130 configuration. For example, as discussed in greater detail below, the inlet 120 and outlet 130 may be off-set from one another such that their respective axes are spaced apart from one another, at an angular with respect to one another, or otherwise not aligned with one another.

In addition to the fluid bag, in some applications (e.g., in critical care applications), it may be necessary to monitor the arterial or venous pressure of the patient (e.g., the intra-arterial blood pressure at the insertion site of the catheter). Therefore, in some instances, the fluid transfer set may also include a pressure transducer (not shown) with a strain gauge that measures the pressure within the artery, converts it into an electrical signal, and forwards the signal to a monitor that plugs into the transducer. The monitor, in turn, may display a graphic representing the intra-arterial blood pressure of the patient.

Figure 2A:
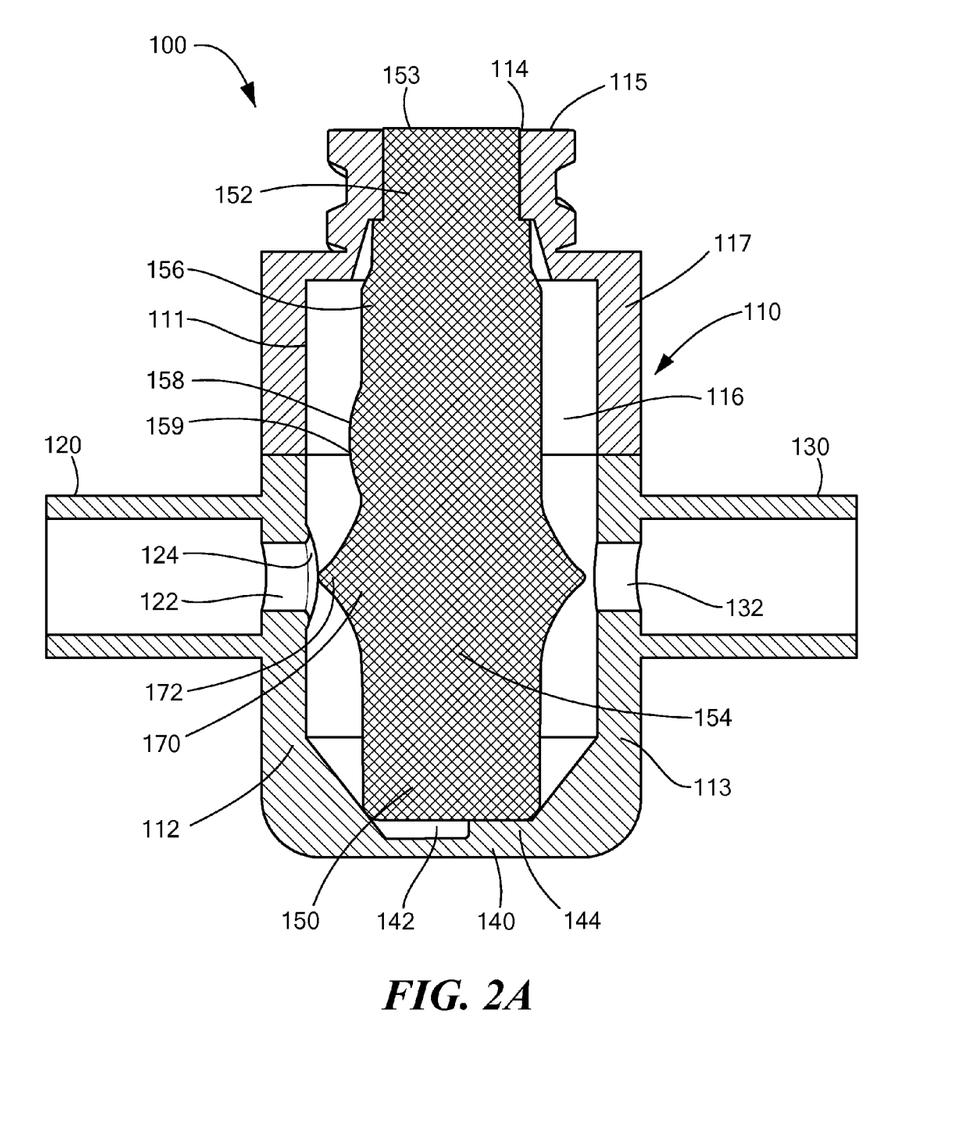
FIG. 2A schematically shows a cross-sectional side view of the sampling port shown in FIG. 1A along line A-A and in the closed mode, in accordance with various embodiments of the present invention.

The body 112 of the hub 110 may include a distal portion 113 and a proximal portion 117 that, when secured together, form a hub chamber 116 within the interior of the body 112 (FIG. 2A). To allow a medical practitioner to take a sample, the sampling port 100 may also include a proximal opening 114 within the hub 110 (e.g., within the proximal portion 117 of the body 112). The proximal opening 114 is capable of receiving a medical implement (e.g., a Luer, needleless syringe, blunt cannula, etc.) that can be used to draw a sample from the sampling port 100.

As best shown in FIG. 2A, the sampling port 100 also has an elastomeric valve member 150 within the hub chamber 116 to seal the proximal opening 114 when in the closed mode. The valve member 150 may include a proximal portion 152 and a distal portion 154 that extends from the proximal portion 152 within the hub chamber 116. As also shown in FIG. 2A, the valve member 150 may be a solid resilient member that extends from the proximal opening 114 to the base 140 of the hub body 112 (e.g., the bottom of the hub chamber 116). As discussed in greater detail below, the bottom of the valve member 150 (e.g., the bottom 155 of the distal portion 154) may interact with base 140 of the hub body 112 to control the deformation of the valve member 150 as the medical port 100 transitions from a closed mode to an open mode, and restrict rotational movement of the valve member 150.

In some embodiments, the proximal portion 152 and/or the proximal surface 153 of the valve member 150 may be flush with or extend slightly above the exterior face 115 of the proximal opening 114 (FIGS. 1A and 2A) of the hub 110. The proximal surface 153 (and/or the proximal portion 152), and the exterior inlet face 115 thus present a swabbable surface, i.e., it may be easily wiped clean with an alcohol swab, for example, or other swab.

Figure 2B:
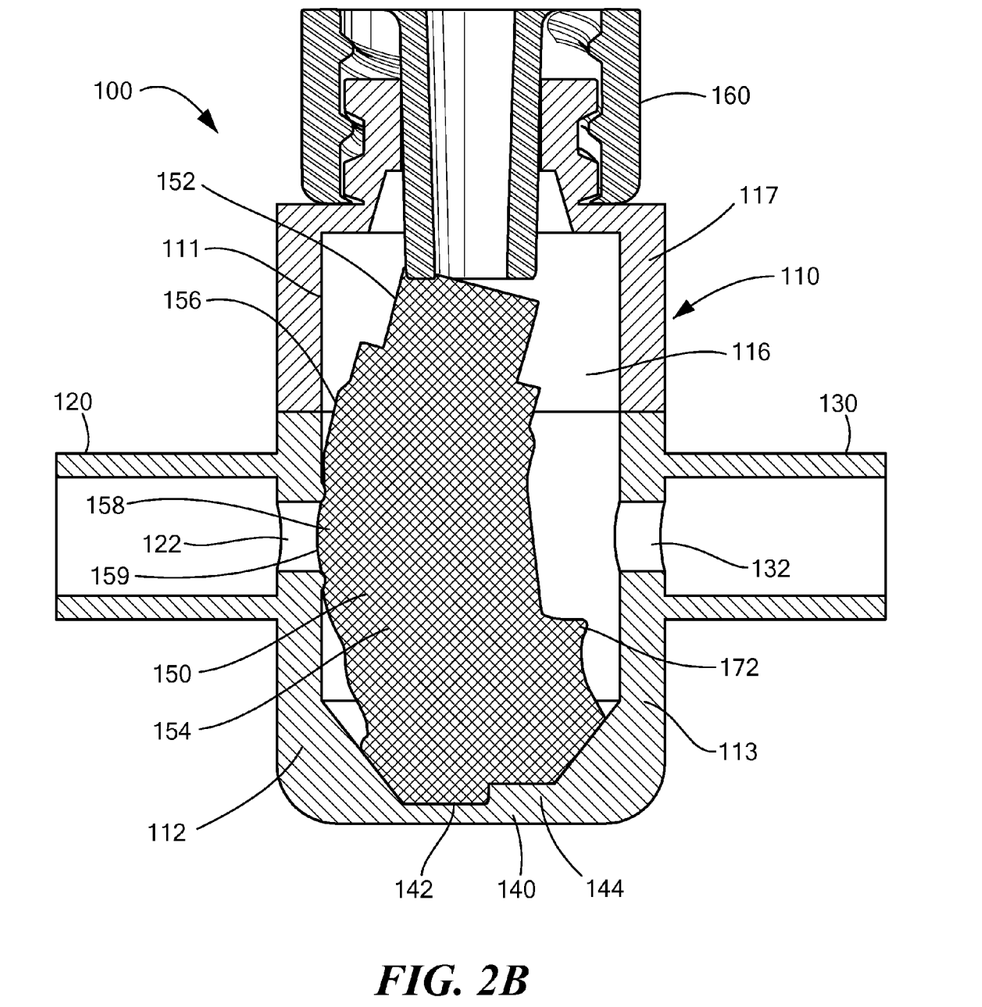
FIG. 2B schematically shows a cross-sectional side view of the sampling port shown in FIG. 1A along line A-A and in the open mode, in accordance with various embodiments of the present invention.

During operation (e.g., when taking a sample via the medical port 100), the medical practitioner may insert a medical implement 160 (FIG. 2B) into the proximal opening 114 of the hub 110. As the medical implement 160 is inserted, the valve member 150, which normally closes the proximal opening 114, moves/deforms distally within the hub chamber 116. As the valve member 150 continues to move/deform distally into the hub chamber 116, the valve member 150 will begin to deform towards one of the radial fluid channels. For example, as shown in FIG. 2B, as the medical implement 160 is inserted, the valve member 150 may deform towards the inlet 120 (e.g., the first radial fluid channel). Alternatively, in some embodiments, the valve member 150 may deform towards the outlet 130 (e.g., the second radial fluid channel).

When the medical/sample port 100 is in the open mode (e.g., shown in FIG. 2B), the valve member 150 may restrict fluid communication in and out of the inlet 120. To that end, a radial portion 156 of the valve member 150 may have an interacting surface 158 that contacts an inner wall 111 of the hub body 112 (e.g., the interacting surface 158 may be pressed against the inner wall 111) such that it at least partially surrounds and/or contacts the opening 122 of the inlet 120. In this manner, the interacting surface 150 can restrict fluid flow in and out of the inlet 120 (e.g., in and out of the opening 122 of the inlet 120). It is important to note that in some embodiments, the interacting surface 150 can prevent fluid flow in and out of the inlet 120 (e.g., the interacting surface may seal the opening 122 of the inlet 120). However, in other embodiments, the interacting surface 150 may merely restrict fluid flow in an out of the inlet 120 to such an extent that a sample may be taken via the proximal opening 114, outlet 130, and medical implement 160 without drawing in fluid contained within the inlet 120/first radial fluid channel.

In some embodiments, the interacting surface 158 may include a rounded protrusion 159 (FIG. 2A) that is approximately the same size and shape as the inlet 120 and/or the opening 122 to the inlet 120. In such embodiments, the valve member 150 may be oriented in the port 100 such that the interacting surface 158 is facing the inlet port 120 to facilitate the interaction between the interacting surface 158 and the inlet 120/opening 122 as the port 100 transitions from the closed mode shown in FIG. 2A to the open mode shown in FIG. 2B.

Although the interacting surface 158 is described above as having a rounded protrusion 159, in other embodiments, the interacting surface 158 may otherwise be contoured or may simply be a flat surface on the valve member 150. To further help restrict the fluid flow, in some embodiments, the inner wall 111 of the hub chamber 116 may receive at least a portion of the interacting surface 158 within the opening 122 of the inlet 120. Additionally or alternatively, the opening 122 (or the inner wall 11 of the hub body 112) may have a protrusion 124 that extends around the opening 122 and receives, mates with or otherwise interacts with at least a portion of the interacting surface 158. In further embodiments, the opening 122 and/or the inner wall 111 of the hub body 112 may have an inset, a lip, a chamfer or similar structure (not shown) that receives, mates with and/or otherwise interacts with the interacting surface 158 of the valve member 150.

As mentioned above, the valve member 150 may deform/collapse toward the inlet 120 of the medical port 100 such that the interacting surface 158 restricts the fluid flow into and out of the inlet 120. To that end, the base 140 of the hub body 112 may be non-symmetrical so that the reaction forces from the base 140 encourage the valve member 150 to deform/collapse toward the inlet 120. For example, the base 140 may have recessed portion 142 located on the same side as the inlet 120, and/or a raised portion 144 located on the opposite side of the inlet 120 (e.g., on the same side as the outlet 130). In such embodiments, as the port 100 transitions from the closed mode to the open mode, the raised portion 144 will exert a greater compressive force along the side of the valve member 150 opposite the inlet 120 (e.g., as compared to the force that the recessed area 142 applies to the side of the valve member 150 on the inlet side). This increased compressive force creates instability within the valve member 150 and causes the valve member 150 (e.g., the elastomeric valve member 150) to collapse toward the inlet 120. This, in turn, will cause the interacting surface 158 to move toward the inlet 120 and restrict the fluid flow between the hub chamber 116 and the inlet 120. The base 140 of the hub body 112 (and its interaction with the distal portion of the valve member 150) may also help to prevent the valve member 150 from rotating within the hub body 112.

Furthermore, in some embodiments, the inner wall 111 of the hub body 112 may help to align the interacting surface 158 with the opening 122 as the valve member 150 collapses toward the inlet 120. For example, the inner wall 111 may be shaped to guide the valve member 150 toward the inlet 120 and align the interacting surface 158 with the opening 122. Alternatively or in addition, the valve member 150 may have alignment ribs (not shown) or otherwise be shaped to help align the interacting surface 158 with the opening 122.

Some embodiments of the valve member 150 may also include features that improve flushing of the hub chamber 116 as fluid flows through the chamber 116 from the inlet 120 to the outlet 130 (e.g., when the port 100 is in the closed mode). For example, as shown in FIG. 2A, the valve member 150 may have a flow disrupter 170 that interacts with the fluid flowing into the hub chamber 116 via the inlet 120 to direct fluid away from the path along the longitudinal axis formed by the inlet 120/first radial fluid channel. In other words, the flow disrupter 170 may direct the fluid proximally and/or distally within the chamber 116 to improve flushing. In some embodiments the flow disrupter 170 may include a tapered ring 172 that extends outwardly from the radial portion 156 of the valve member 150. In such embodiments, as the fluid hits the tapered ring 172, some of the fluid is directed proximally to flush the top portion of the hub chamber 116 and some of the fluid is directed distally to flush the bottom port.

In addition to the pressure transducer mentioned above, some fluid transfer sets may include a reservoir (not shown) upstream of the hub chamber 116. Prior to taking a sample and/or inserting the medical implement 160 into the proximal opening 114, fluid located within the chamber 116 may be drawn into the reservoir to prime the chamber 116 with blood (e.g., so that the medical practitioner obtains an undiluted sample of blood). In such embodiments, in addition to interacting with the fluid flowing into the hub chamber 116 via the inlet 120, the flow disrupter 170 may also interact with the fluid flowing into the hub chamber 116 via the outlet 130, such as to improve the filling of the hub chamber 116 with blood that is drawn from the patient into the upstream portion of the monitoring line in preparation for drawing a blood sample from the sampling port 100.

It is important to note that, although the flow disruption feature 170 shown in FIG. 2A is a tapered ring 172 continuously formed around the valve member 150, other embodiments may have different flow disruption features. For example, some embodiments may have a discontinuous ring, and/or a ring with a different cross-sectional shape (e.g., it may not be tapered). Additionally or alternatively, as discussed in greater detail below, the flow disruption feature 170 may be a helical groove (or a helical protrusion) around the valve member 150. Also, in some embodiments, the flow disruption feature 170 may be part of the interacting surface 158 and/or may be formed at least partially by the alignment ribs on the valve member 150.

Figure 3:
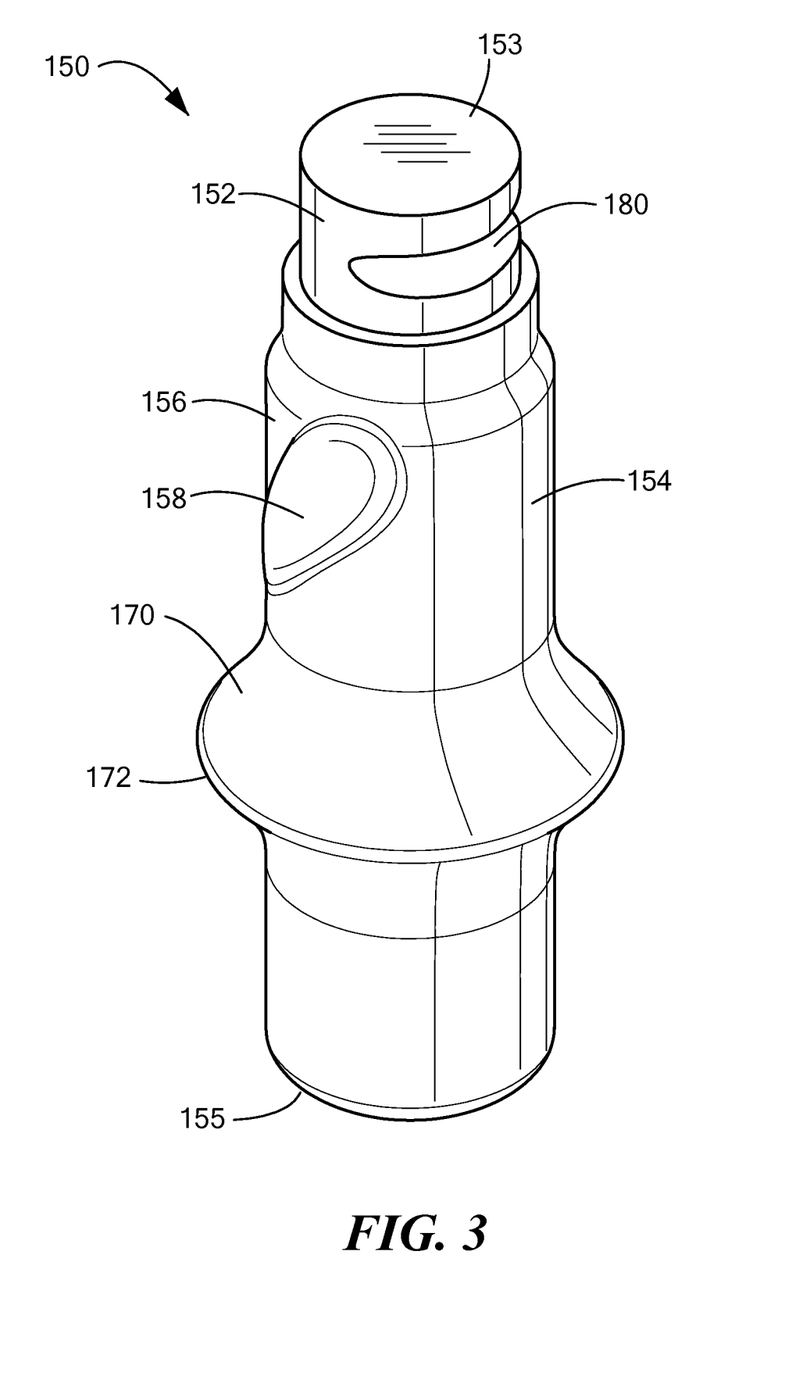
FIG. 3 schematically shows a perspective view of an alternative valve member for use in the sampling port shown in FIG. 1A, in accordance with various embodiments of the present invention.
Figure 4A:
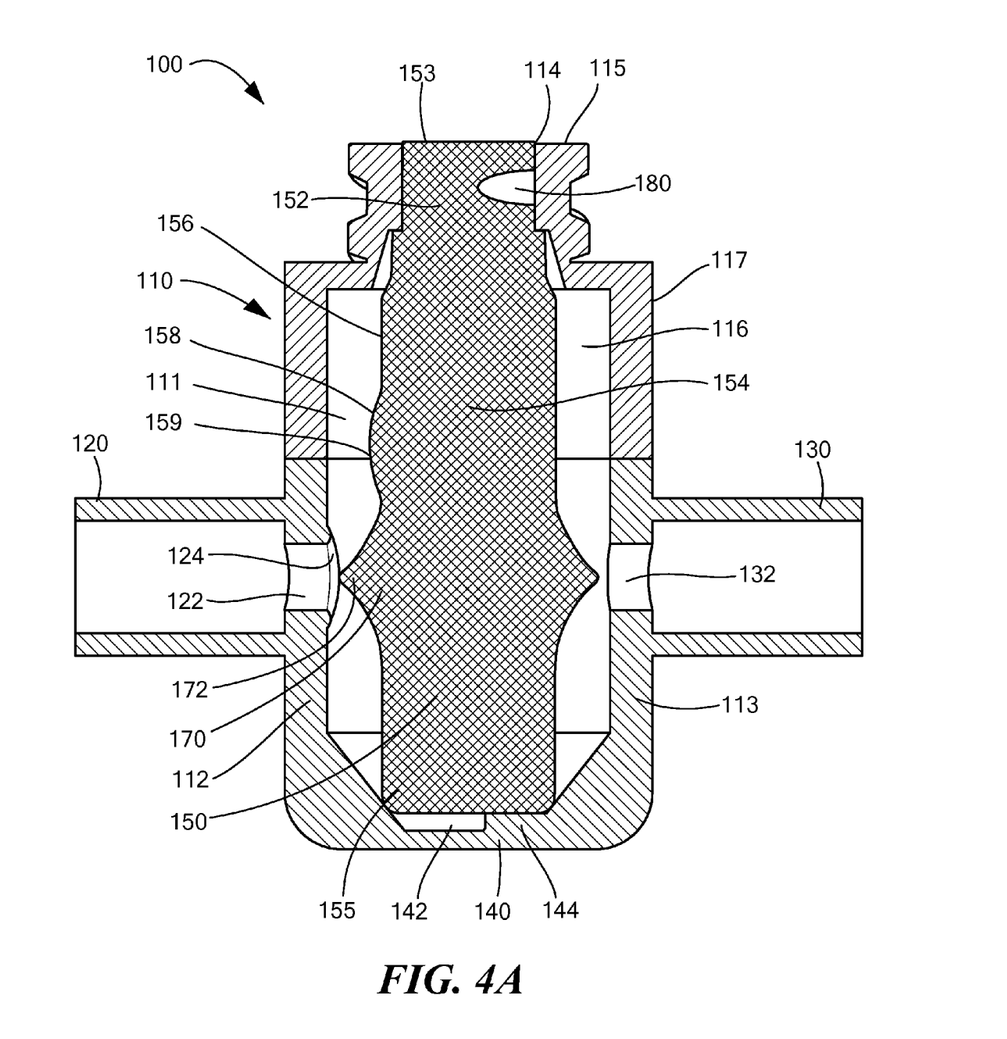
FIG. 4A schematically shows a cross-sectional side view of the sampling port shown in FIG. 1A along line A-A, in the closed mode, and with the alternative valve member shown in FIG. 3, in accordance with various embodiments of the present invention.
Figure 4B:
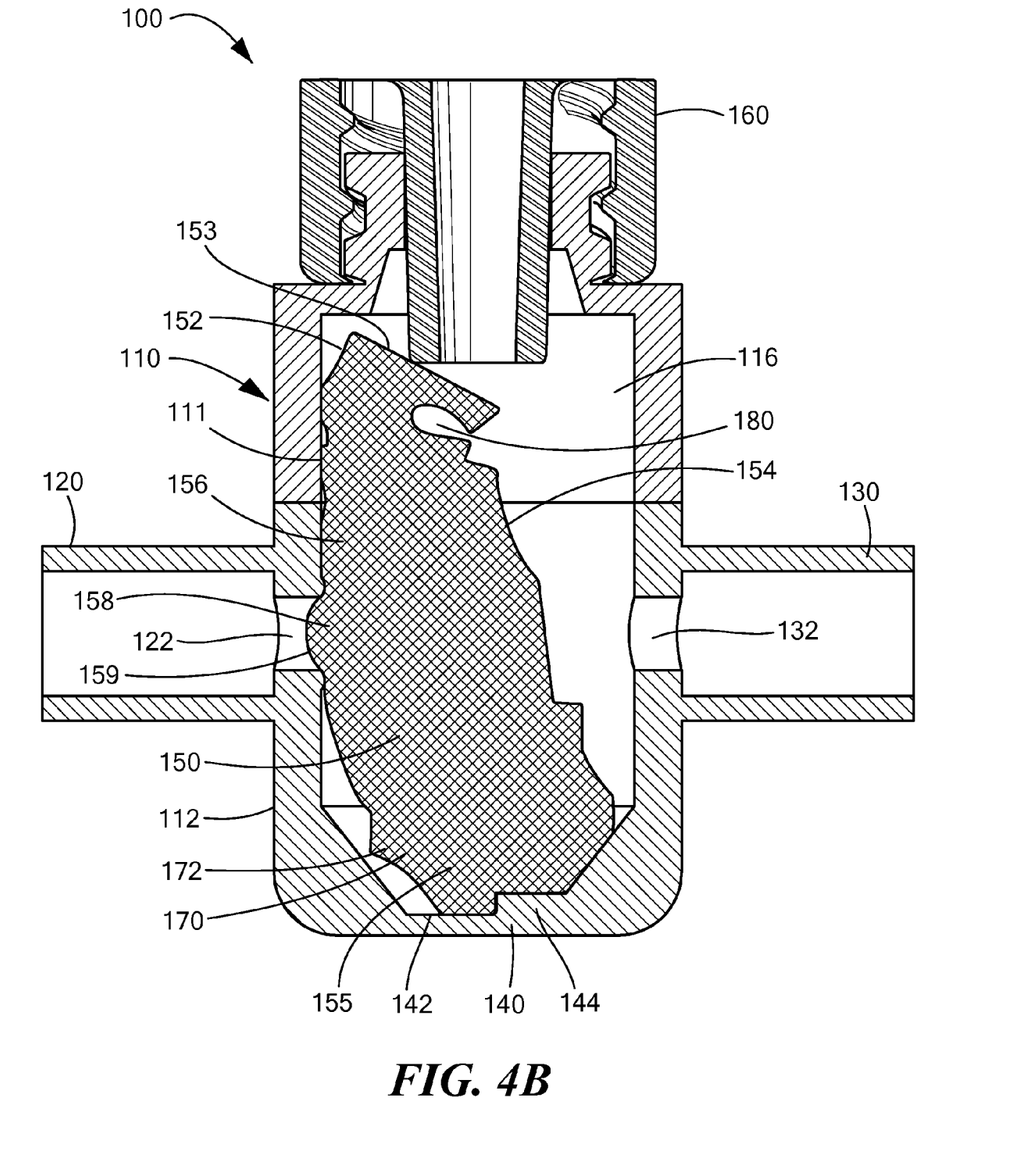
FIG. 4B schematically shows a cross-sectional side view of the sampling port shown in FIG. 1A along line A-A, in the open mode, and with the alternative valve member shown in FIG. 3, in accordance with various embodiments of the present invention.

In addition to the non-symmetrical base 140 discussed above, some embodiments may have additional features that aid in the collapse/deformation of the valve member 150. For example, as shown in FIG. 3, the valve member 150 may have a notch 180 and/or a cut-out within the proximal portion 152 of the valve member 150 (e.g., adjacent to the proximal face 153). In such embodiments, as the medical implement 160 is inserted into the proximal opening 114, the valve member 150 will collapse and deform in a manner similar to that discussed above. However, in addition, the proximal portion 152 of the valve member 150 will collapse at the notch 180 causing further deformation of the valve member 150. In some embodiments, the further deformation will cause more of the valve member 150 to contact the inner wall 111 of the hub body 112 (FIG. 4B). This, in turn, will help restrict the fluid flow in and out of the inlet 120 and facilitate fluid communication between the medical implement 160 and the outlet 130.

Figure 5:
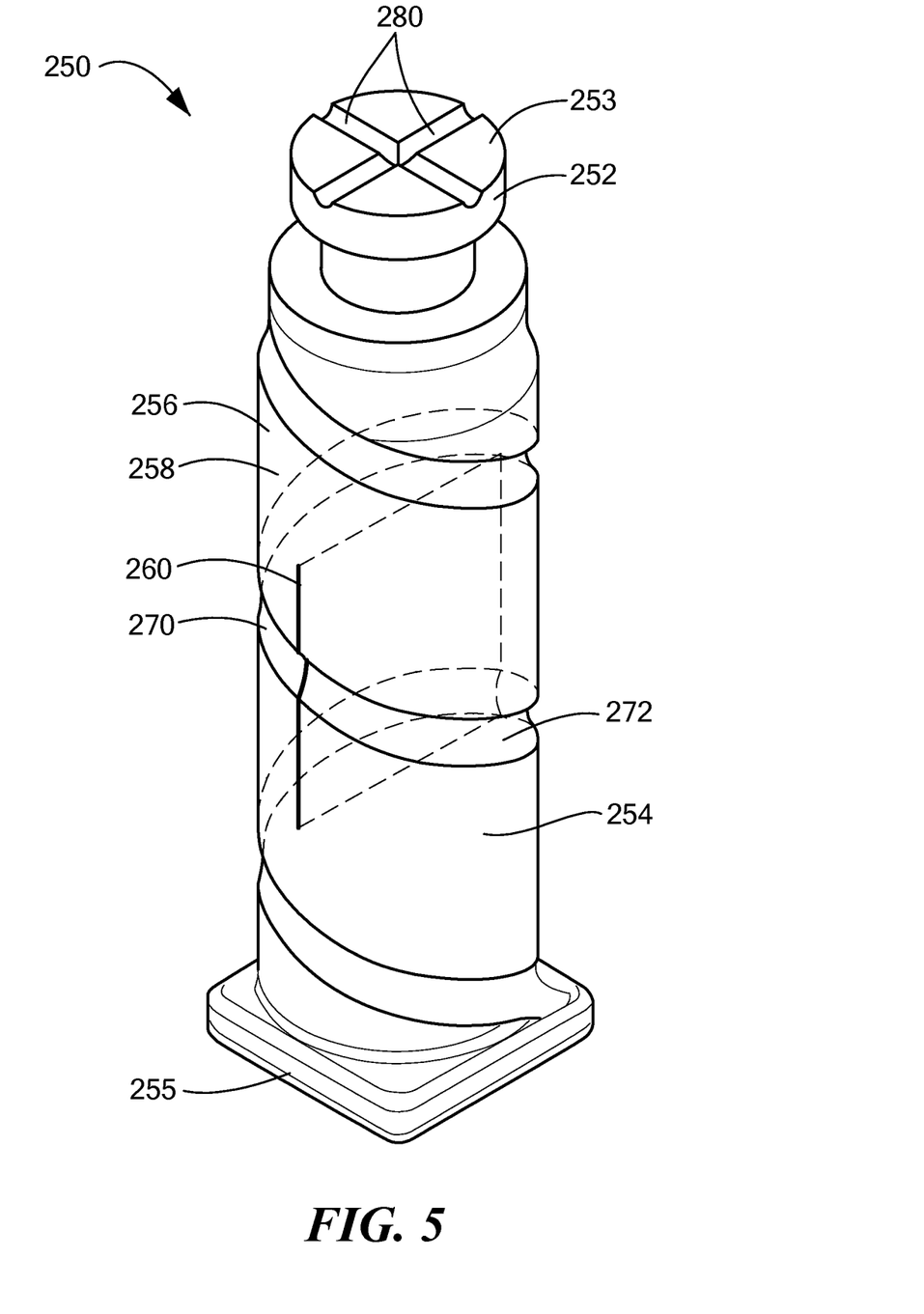
FIG. 5 schematically shows a perspective view of an additional alternative valve member for use in a sampling port, in accordance with additional embodiments of the present invention.

FIG. 5 schematically shows an alternative valve member 250 that may be used in conjunction with the medical port 100 discussed above and/or the alternative medical port 200 shown in FIGS. 6A and 6B (discussed in greater detail below). Like the valve member 150 discussed above, the valve member 250 shown in FIG. 5 may have a proximal portion 252, a distal portion 254, and a radial portion 256 that interacts with the inlet 220 (e.g., the opening 222 of the inlet 220) to restrict the fluid flow between the inlet 220 and the hub chamber 216 when the port 200 is in the open mode (FIG. 6B). Additionally, the valve member 250 may also have a flow disrupter 270 that disrupts/interacts with the fluid flow between the inlet 220 and outlet 230 (or between the outlet 230 and the inlet 220) and improves flushing. For example, the flow disrupter 270 may be helical groove 272 (or a helical protrusion) that is circumferentially formed within/on the surface of the valve member 250. The helical flow disrupter 270 may be aligned with or orthogonal to a line connecting the inlet opening 122 and the outlet opening 132. The pitch, width, height, depth, and number of helical structures may vary depending on the application and the amount of flushing required.

The valve member 250 may also have a slit 260 that extends through the width of the valve member 250 and along/parallel to the length of the valve member 250. As will be discussed in greater detail below, the slit 260 may be closed (or substantially closed) when the medical/sampling port 200 is in the closed mode (FIG. 6A) and may open as the medical/sampling port 200 transitions to the open mode (FIG. 6B). In some embodiments, the slit 260, when in the open mode, may form part of the fluid path between the proximal opening 214 and the outlet 220. Additionally or alternatively, the slit 260 may have a proximally extending portion (or the valve member 250 may have a second proximally extending slit) that extends proximally toward and through the proximal face 153 of the valve member 150. In such embodiments, during fluid transfer, fluid may enter the slit 260 and flow up into the proximally extending portion (or the second slit) and into the medical implement.

As mentioned above, to ensure that the radial portion of the valve member 250 is able to restrict fluid flow in/out of the inlet 220, it useful to prevent the valve member 250 from significantly rotating within the hub body 212. To that end, the distal end 254 of the valve member 250 and the base 240 of the hub body 212 may be sized and shaped to rotationally constrain the valve member 250. For example, the distal end 254 may be square and the base 240 of the hub body 212 may have a corresponding square shaped recess 242 in which the bottom 255 of the distal end 254 of the valve member 250 resides. It is important to note that, although the base 240 of the hub body 212 and the distal end 254 of the valve member 250 are described above as having a square shape, other embodiments may utilize different shapes. For example, the base 240 and distal end 254 may be rectangular, triangular, polygonal, to name but a few.

To help facilitate fluid flow between the hub chamber 216 and the medical implement 160, the proximal surface 253 of the valve member 250 may have features that allow fluid to flow more easily. For example, the valve member 250 may have one or more channels 280 (FIG. 5) formed within the proximal surface 253 and through which the fluid may flow. The channels 280 may be formed in the proximal surface 253 of the valve member or may be made from a different material (e.g., a rigid thermoplastic) that is adhered to or over-molded on the valve member 250. Additionally or alternatively, the valve member 250 may have raised features or ribs (not shown) to help facilitate the fluid flow between the hub chamber 216 and the medical implement 160. Also, it is important to note that, although FIG. 5 shows two channels 280 in a cross pattern, other embodiments can have more (greater than two) or less (e.g., one) channels 280, and the channels 280 may vary in shape, depth, and configuration depending on the application.

During operation of the medical port 200, the medical practitioner may insert a medical implement 160 into the proximal opening 214 and begin to move the medical implement 160 distally within the hub body 212. As the medical implement 160 is moved distally, the valve member 250 will begin to deform and collapse. However, unlike the embodiment shown in FIG. 3 (which deforms non-uniformly), as shown in FIG. 6B, the valve member 250 may deform uniformly, and the slit 260 will open. This, in turn, causes the width of the valve member 250 to increase and the radial portion 256 of the valve member 250 to interact with the opening 222 of the inlet 220. For example, the radial portion 256 (e.g., an interacting surface 258) of the valve member 250 may restrict and/or prevent fluid communication in and out of the inlet 220 in a manner similar to that described above.

Once the medical port 200 is in the open mode (shown in FIG. 6B) and the flow in/out of the inlet 220 is restricted, the medical practitioner may draw a sample using the medical implement 160. In some embodiments, the open slit 260 may form part of the fluid path between the outlet 230 and the medical implement 160. For example, as the medical practitioner takes the sample, fluid may flow from the outlet 230, into the hub chamber 216, through the open slit 260, back into the hub chamber 216, and into the medical implement 160 located within the proximal opening 214. Additionally, if the valve member 150 includes the proximally extending portion of the slit 260 (or the second slit), the fluid may flow from the outlet 230, into the hub chamber, through the open slit 260 and the proximally extending portion of the slit, and into the medical implement 160. However, in other embodiments, the open slit 260 may not form part of the flow path and the fluid will flow from the outlet 230, into the hub chamber 216, and into the medical implement 160 within the proximal opening 214.

Figure 6A:
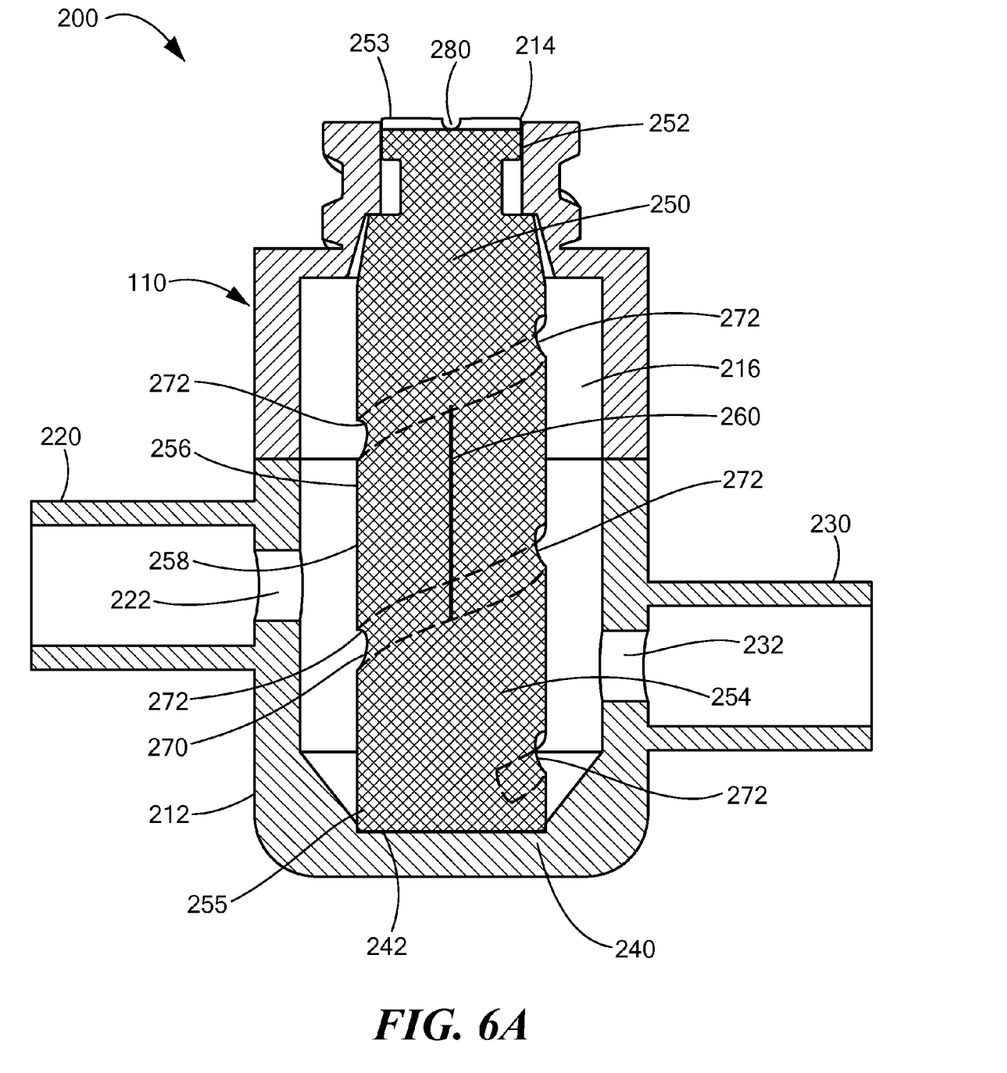
FIG. 6A schematically shows a cross-sectional side view of an alternative sampling port in the closed mode and using the alternative valve member shown in FIG. 5, in accordance with various embodiments of the present invention.
Figure 6B:
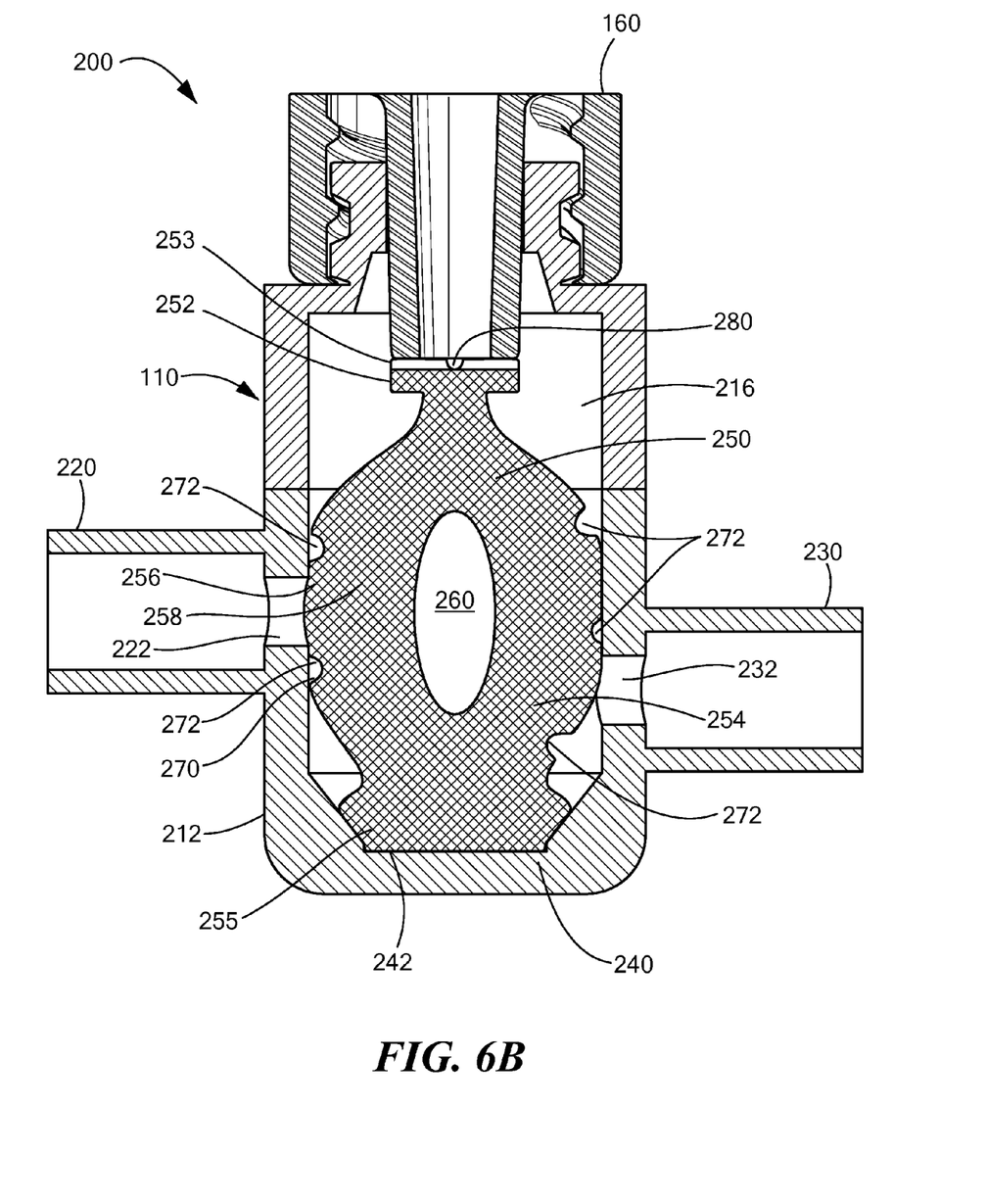
FIG. 6B schematically shows a cross-sectional side view of the alternative sampling port shown in FIG. 6A using the alternative valve member shown in FIG. 5 and in the open mode, in accordance with various embodiments of the present invention.

As mentioned above, the valve member 250 may deform uniformly as medical port 200 transitions from the closed mode shown in FIG. 6A to the open mode shown in FIG. 6B. To ensure that the radial portion 256 (or any other portion) of the valve member 250 does not restrict or block fluid flow in/out of the outlet 230, in some embodiments, the inlet 220 and outlet 230 may be off-set from one another such that the inlet 220 and outlet 230 are located different distances away from the base 240 of the hub body 212. For example, as shown in FIGS. 6A and 6B, the inlet 220 (e.g., the opening 222 of the inlet 220) may be located further away from the base 240 as compared to the outlet 230 (e.g., the opening 232 of the outlet 230). Alternatively, the inlet 220 (e.g., the opening 222 of the inlet 220) may be located closer to the base 240 as compared to the outlet 230 (e.g., the opening 232 of the outlet 230).

It should be understood that the various embodiments of the sampling ports 100/200 described above provide numerous advantages over prior art sampling ports. Among others, under expected fluid flow rates such as while the transfer set is being flushed with fluid from a pressurized fluid bag and the sampling port 100/200 is in the closed mode, the design disrupts the fluid flow to fully flush the interior of hub chamber 116/216. This improved flushing is accomplished without the need for the practitioner to manipulate or otherwise move the sample port 100/200—it thus may be considered to be "self-flushing". This is in contrast to prior art stopcock designs, which require rotational manipulation of the various flow paths within their systems.

Further, the sampling port 100/200 ensures that a more accurate fluid sample is taken. For example, as discussed above, various embodiments of the present invention restrict the fluid flow from the inlet 120/220 of the sampling port 100/200 when in the open mode. This, in turn, prevents stagnant and/or diluted fluid from being drawn from the inlet 120/220 and contaminating the fluid sample being taken—it thus may be considered to be "self-closing". This is in contrast to prior art stopcock designs, which require rotational manipulation of the various flow paths within their systems to restrict upstream fluid flow.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A medical port having an open mode that permits fluid transfer and a closed mode that prevents fluid transfer, the medical port comprising:
   a hub having a body forming a hub chamber for containing a fluid, the hub further having a proximal opening to the hub chamber for receiving a medical implement;
   a valve member located within the hub chamber and having a radial portion, the valve member configured to close the proximal opening when the medical port is in the closed mode, at least a portion of the valve member being resilient
   a first radial fluid channel having a first radial fluid channel opening into the hub chamber, the first radial fluid channel in fluid communication with the hub chamber when the medical port is in the closed mode, the radial portion of the valve member configured to restrict fluid communication between the first radial fluid channel and the hub chamber when the medical port is in the open mode; and
   a second radial fluid channel having a second radial fluid channel opening into the hub chamber, the second radial fluid channel in fluid communication with the hub chamber when the medical port is in the closed mode and in the open mode, at least a portion of the valve member within the hub chamber located between the first radial fluid channel opening and the second radial fluid channel opening when the medical port is in the closed mode.

2. A medical port according to claim 1, wherein the radial portion is configured to fluidly disconnect the first radial fluid channel and the hub chamber when the medical port is in the open mode.

3. A medical port according to claim 1, wherein the valve member includes a flow disrupter configured to interact with fluid entering the hub chamber when the medical port is in the closed mode to flush the hub chamber.

4. A medical port according to claim 3, wherein the flow disrupter comprises at least one selected from the group consisting of a ring extending radially outward from the valve member, a helical groove within the valve member, and a raised helical structure within the valve member.

5. A medical port according to claim 1, wherein the first radial fluid channel is aligned with the second radial fluid channel.

6. A medical port according to claim 1, wherein the first radial fluid channel is offset from the second radial fluid channel such that the first radial fluid channel is located a first distance from a base of the body of the hub and the second radial fluid channel is located a second distance from the base, the first distance being different than the second distance.

7. A medical port according to claim 1, wherein the first and second radial fluid channels are in fluid communication with each other when the medical port is in the closed mode.

\* \* \* \* \*